(12) United States Patent
Hamaguchi et al.

(10) Patent No.: US 10,022,075 B2
(45) Date of Patent: Jul. 17, 2018

(54) BIOLOGICAL INFORMATION MEASUREMENT DEVICE

(71) Applicant: OMRON HEALTHCARE CO., LTD., Muko-shi, Kyoto (JP)

(72) Inventors: Takehiro Hamaguchi, Kyoto (JP); Hiromichi Karo, Kyoto (JP); Junichi Ishida, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 555 days.

(21) Appl. No.: 14/741,507

(22) Filed: Jun. 17, 2015

(65) Prior Publication Data

US 2015/0282748 A1    Oct. 8, 2015

Related U.S. Application Data (63) Continuation of application No. PCT/JP2013/080980, filed on Nov. 18, 2013.

(30) Foreign Application Priority Data

Dec. 20, 2012  (JP) ................................ 2012-278343

(51) Int. Cl.
*A61B 5/1455*    (2006.01)
*A61B 5/00*    (2006.01)
*A61B 5/024*    (2006.01)

(52) U.S. Cl.
CPC ...... *A61B 5/14552* (2013.01); *A61B 5/14551* (2013.01); *A61B 5/6826* (2013.01);
(Continued)

(58) Field of Classification Search
CPC ... A61B 5/0205; A61B 5/0059; A61B 5/1455; A61B 5/14551; A61B 5/14552;
(Continued)

(56) References Cited

U.S. PATENT DOCUMENTS 5,490,523 A * 2/1996 Isaacson ............ A61B 5/02427
600/323
5,766,127 A * 6/1998 Pologe ................. A61B 5/0261
600/310

(Continued)

FOREIGN PATENT DOCUMENTS

| JP | 02-036840 A | 2/1990 |
| JP | 2004-535248 A | 11/2004 |
| JP | 2008-532589 A | 8/2008 |
| JP | 2012-508609 A | 4/2012 |

OTHER PUBLICATIONS

Official Communication issued in International Patent Application No. PCT/JP2013/080980, dated Dec. 10, 2013.

(Continued)

*Primary Examiner* — Eric Winakur
*Assistant Examiner* — Chu Chuan (JJ) Liu
(74) *Attorney, Agent, or Firm* — Keating and Bennett, LLP (57) ABSTRACT

A biological information measurement device according to the present invention detects a signal expressing biological information from a fingertip using an internal sensor (S1). A first perfusion index and first biological information aside from the first perfusion index are obtained from the signal detected by the internal sensor (S2, S3). It is determined whether or not the first perfusion index is greater than or equal to a first threshold (S4). When the first perfusion index is greater than or equal to the first threshold, the first biological information is permitted to be displayed in a display unit (S5). However, when the first perfusion index is less than the first threshold, a notification is made indicating that an external sensor that is lighter than a main body, is an entity separate from the main body, and is communicably connected to the main body is to be used (S6).

9 Claims, 7 Drawing Sheets

(52) U.S. Cl.
CPC ........ *A61B 5/7445* (2013.01); *A61B 5/02433* (2013.01); *A61B 2560/0266* (2013.01); *A61B 2560/0443* (2013.01)

(58) Field of Classification Search
CPC ..... A61B 5/14553; A61B 5/68; A61B 5/6801; A61B 5/6802; A61B 5/6826; A61B 5/7445; A61B 5/02433
See application file for complete search history.

(56) References Cited

U.S. PATENT DOCUMENTS

| | | | | |
|---|---|---|---|---|
| 6,006,120 | A * | 12/1999 | Levin .................. | A61B 5/14552 600/323 |
| 6,334,065 | B1 * | 12/2001 | Al-Ali ................ | A61B 5/14551 600/323 |
| 2006/0009687 | A1 * | 1/2006 | De Felice .......... | A61B 5/14551 600/323 |
| 2010/0121164 | A1 * | 5/2010 | Donars .............. | A61B 5/14551 600/323 |
| 2013/0053663 | A1 * | 2/2013 | Sivonen .............. | A61B 5/6843 600/323 |
| 2013/0096405 | A1 * | 4/2013 | Garfio ................ | A61B 5/14552 600/340 |

OTHER PUBLICATIONS www.nissei-kk.com.jp/html/bo800dx.html, "Fingertip Clip-Type Pulse Oximeter PulsFit BO-800DX," Japan Precision Instructions, Inc., downloaded Nov. 26, 2012, 4 pages.

* cited by examiner

BIOLOGICAL INFORMATION MEASUREMENT DEVICE

TECHNICAL FIELD

This invention relates to biological information measurement devices, and particularly relates to biological information measurement devices that include, in a main body that is to be attached to a measurement area, a sensor that detects a signal expressing biological information from the measurement area.

BACKGROUND ART

The fingertip clip-type pulse oximeter "PulsFit BO-800DX", manufactured by Japan Precision Instruments, Inc., is known as a conventional example of this type of biological information measurement device (see Non-Patent Literature 1, for example). This fingertip clip-type pulse oximeter includes a sensor that detects a signal expressing a transdermal oxygen saturation level ($SpO_2$) in arterial blood serving as biological information from a fingertip, which serves as a measurement area, and a display unit that displays the $SpO_2$ value, in a main body that holds the fingertip. Dry cell batteries (two, size AAA) are installed in the main body as a power source.

CITATION LIST

Non-Patent Literature

Non-Patent Literature 1: Japan Precision Instruments, Inc., "Fingertip Clip-type Pulse Oximeter PulsFit BO-800DX", on sale February 2010 (online); retrieved Nov. 26, 2012, from http://www.nissei-kk.co.jp/html/bo800dx.html

SUMMARY OF INVENTION

Technical Problem

In the above fingertip clip-type pulse oximeter, dry cell batteries or the like are installed in the main body, resulting in a comparatively high mass. As such, the fingertip serving as the measurement area is pressurized by the mass of the main body in addition to the holding pressure of the main body (a clip pressure). Thus when measuring the $SpO_2$ of, for example, a patient having a serious condition, there are cases where there is insufficient blood flow to the fingertip, which causes hypoperfusion; as a result, an accurate measurement cannot be taken and an inaccurate $SpO_2$ value is obtained.

Here, the conventional pulse oximeter displays the obtained $SpO_2$ value regardless of whether or not there is hypoperfusion. There is thus a problem that an inaccurate $SpO_2$ value being displayed will cause a user (medical staff such as a doctor or a nurse, a measurement subject, or the like; the same applies hereinafter) to make errors in his/her judgment.

Because the aforementioned fingertip clip-type pulse oximeter has a comparatively high mass, reducing the pressure of the clip results in problems such as the position of the sensor relative to the measurement area shifting and causing inaccurate measurements, or the sensor falling off the measurement area along with the main body. Thus reducing the clip pressure cannot be called a useful solution.

Accordingly, it is an advantage of this invention to provide a biological information measurement device including, in a main body that is to be attached to a measurement area, a sensor that detects a signal expressing biological information from the measurement area, that prompts a user to take a measurement accurately.

Solution to Problem

To achieve the aforementioned advantage, a biological information measurement device according to this invention has a main body that is to be attached to a measurement area, the device including, in the main body: a first sensor that detects a signal expressing biological information from the measurement area; a display unit capable of displaying biological information; a first perfusion index obtainment unit that obtains a first perfusion index expressing a ratio between a pulsation component and a non-pulsation component of arterial blood in the measurement area based on the signal detected by the first sensor; a first biological information obtainment unit that obtains first biological information of the measurement area, aside from the first perfusion index, by processing the signal detected by the first sensor; a first determining unit that determines whether or not the first perfusion index is greater than or equal to a first threshold; and a control unit that carries out control for permitting the first biological information to be displayed in the display unit when the first determining unit has determined that the first perfusion index is greater than or equal to the first threshold and making a notification that a second sensor that is lighter than the main body, is an entity separate from the main body, and is communicably connected to the main body is to be used when the first determining unit has determined that the first perfusion index is less than the first threshold.

In the present specification, "perfusion index" (PI) is expressed as follows, using a ratio between the pulsation component and the non-pulsation component of the signal detected by the sensor:

$$PI(\%)=(\text{pulsation component})/(\text{non-pulsation component})\times 100$$

The PI normally has a value within a range of 0.02% to 20%, and greater than or equal to 1% is considered a desirable value (for example, see Katsuaki Tanaka, "21st Symposium of Japan Association for Clinical Monitoring—Perfusion Index and Pleth Variability Index", The Journal of Japan Society for Clinical Anesthesia, Vol. 31, No. 2, pp. 347-352; March, 2011).

Note that a transdermal oxygen saturation level of arterial blood ($SpO_2$), a pulse rate (BPM (Beats Per Minute)), and a pulse waveform can be given as examples of "biological information" aside from the perfusion index.

Meanwhile, the "threshold" for the perfusion index may be fixed at 1%, for example, or may be set to be variable.

Furthermore, the second sensor being "an entity separate from the main body" and "communicably connected to the main body" means that the second sensor is substantially separate from the main body and that the second sensor is communicably connected to the main body with a wire such as a cable or wirelessly.

In the biological information measurement device according to this invention, the first sensor detects a signal expressing biological information from the measurement area. The first perfusion index obtainment unit obtains the first perfusion index expressing a ratio between a pulsation component and a non-pulsation component of arterial blood in the measurement area based on the signal detected by the first sensor. Along with this, the first biological information obtainment unit obtains the first biological information of the measurement area, aside from the first perfusion index, by processing the signal detected by the first sensor. The first determining unit determines whether or not the first perfusion index is greater than or equal to the first threshold. The first biological information is considered accurate when the first determining unit has determined that the first perfusion index is greater than or equal to the first threshold. At this time, the control unit permits the first biological information to be displayed in the display unit. Accordingly, the user can know the accurate biological information by viewing the first biological information displayed in the display unit. However, the first biological information is considered inaccurate when the first determining unit has determined that the first perfusion index is less than the first threshold. At this time, the control unit carries out control for making a notification that the second sensor that is lighter than the main body, is an entity separate from the main body, and is communicably connected to the main body is to be used. Accordingly, the user is prompted by the notification to use the second sensor to detect the signal expressing the biological information from the measurement area. In other words, the user is prompted to take a more accurate measurement.

In the biological information measurement device according to an embodiment, the control unit prohibits the first biological information from being displayed in the display unit when the first determining unit has determined that the first perfusion index is less than the first threshold.

With the biological information measurement device according to this embodiment, the control unit prohibits the first biological information from being displayed in the display unit when the first determining unit has determined that the first perfusion index is less than the first threshold. Accordingly, the user will no longer be caused to make an error in his/her judgment by inaccurate biological information.

In the biological information measurement device according to an embodiment, the control unit displays an indication that the first perfusion index is low in the display unit when the first determining unit has determined that the first perfusion index is less than the first threshold.

With the biological information measurement device according to this embodiment, the control unit displays an indication that the first perfusion index is low in the display unit when the first determining unit has determined that the first perfusion index is less than the first threshold. Accordingly, the user can recognize that the first perfusion index being low is the reason for the notification indicating that the second sensor is to be used.

The biological information measurement device according to an embodiment further includes a connection detecting unit that detects whether or not the second sensor has been connected to the main body, and a second biological information obtainment unit that obtains second biological information of the measurement area by processing the signal detected by the second sensor from the measurement area when the second sensor has been connected to the main body. Here, when the second biological information has been obtained by the second biological information obtainment unit, the control unit permits the second biological information to be displayed in the display unit.

With the biological information measurement device according to this embodiment, the connection detecting unit detects whether or not the second sensor has been connected to the main body. The second biological information obtainment unit obtains the second biological information of the measurement area by processing the signal detected by the second sensor from the measurement area when the second sensor has been connected to the main body. When the second biological information has been obtained by the second biological information obtainment unit, the control unit permits the second biological information to be displayed in the display unit. Here, the second sensor is external to the main body and is lighter than the main body, and thus less pressure is put on the measurement area than when using the first sensor, which in turn does not interfere significantly with perfusion. Accordingly, the second biological information obtained using the second sensor can be expected to be more accurate than the first biological information obtained using the first sensor.

The biological information measurement device according to an embodiment further includes: a connection detecting unit that detects whether or not the second sensor has been connected to the main body; a second perfusion index obtainment unit that obtains a second perfusion index expressing a ratio between a pulsation component and a non-pulsation component of arterial blood in the measurement area based on the signal detected by the second sensor from the measurement area when the second sensor has been connected to the main body; a second biological information obtainment unit that obtains second biological information of the measurement area, aside from the second perfusion index, by processing the signal detected by the second sensor; and a second determining unit that determines whether or not the second perfusion index is greater than or equal to a second threshold. Here, the control unit carries out control for permitting the second biological information to be displayed in the display unit when the second determining unit has determined that the second perfusion index is greater than or equal to the second threshold and making a notification that an accurate measurement cannot be taken when the second determining unit has determined that the second perfusion index is less than the second threshold.

With the biological information measurement device according to this embodiment, the connection detecting unit detects whether or not the second sensor has been connected to the main body. The second perfusion index obtainment unit obtains the second perfusion index expressing a ratio between a pulsation component and a non-pulsation component of arterial blood in the measurement area based on the signal detected by the second sensor from the measurement area when the second sensor has been connected to the main body. Along with this, the second biological information obtainment unit obtains the second biological information of the measurement area by processing the signal detected by the second sensor. The second determining unit determines whether or not the second perfusion index is greater than or equal to the second threshold. The second biological information is considered accurate when the second determining unit has determined that the second perfusion index is greater than or equal to the second threshold. At this time, the control unit permits the second biological information to be displayed in the display unit. Accordingly, the user can know the accurate biological information by viewing the second biological information displayed in the display unit. However, the second biological information is considered inaccurate when the second determining unit has determined that the second perfusion index is less than the second threshold. At this time, the control unit carries out control for making a notification that an accurate measurement cannot be taken. Accordingly, by viewing this message, the user can know that accurate biological information cannot be obtained from the measurement area for that measurement subject (for example, a patient having a serious level of poor peripheral circulation).

In the biological information measurement device according to an embodiment, the control unit prohibits the second biological information from being displayed in the display unit when the second determining unit has determined that the second perfusion index is less than the second threshold.

With the biological information measurement device according to this embodiment, the control unit prohibits the second biological information from being displayed in the display unit when the second determining unit has determined that the second perfusion index is less than the second threshold. Accordingly, the user will no longer be caused to make an error in his/her judgment by inaccurate biological information.

In the biological information measurement device according to an embodiment, the control unit displays an indication that the second perfusion index is low in the display unit when the second determining unit has determined that the second perfusion index is less than the second threshold.

With the biological information measurement device according to this embodiment, the control unit displays an indication that the second perfusion index is low in the display unit when the second determining unit has determined that the second perfusion index is less than the second threshold. Accordingly, the user can recognize that the second perfusion index being low is the reason for the notification indicating that an accurate measurement cannot be taken.

In the biological information measurement device according to an embodiment, a part including the first sensor is provided so as to be removable from the main body, and the control unit carries out control for making a notification that the part including the first sensor is to be removed from the main body and used instead of a notification indicating that the second sensor is to be used when the first determining unit has determined that the first perfusion index is less than the first threshold.

With the biological information measurement device according to this embodiment, the first sensor is provided so as to be removable from the main body. The control unit carries out control for making a notification that the part including the first sensor is to be removed from the main body and used instead of a notification indicating that the second sensor is to be used when the first determining unit has determined that the first perfusion index is less than the first threshold. Accordingly, the notification prompts the user to remove the part including the first sensor from the main body and use the sensor in that state. The part including the first sensor is lighter than the main body as a whole, and thus little pressure is put on the measurement area, which in turn does not interfere significantly with perfusion. Accordingly, taking a measurement using the part including the first sensor that has been removed from the main body enables a more accurate measurement than in the case where a measurement is taken with the first sensor remaining attached to the main body.

In the biological information measurement device according to an embodiment, the notification is a display of a message or a graphic in the display unit and/or a buzzer sound or audio.

With the biological information measurement device according to this embodiment, the notification is a display of a message or a graphic in the display unit and/or a buzzer sound or audio, and thus the user can easily recognize that there has been a notification and confirm the details of the notification.

Advantageous Effects of Invention

As is clear from the foregoing, according to the biological information measurement device of this invention, a user can be prompted to take an accurate measurement.

DESCRIPTION OF EMBODIMENTS

Hereinafter, an embodiment of the invention will be described in detail with reference to the drawings.

Figure 1:
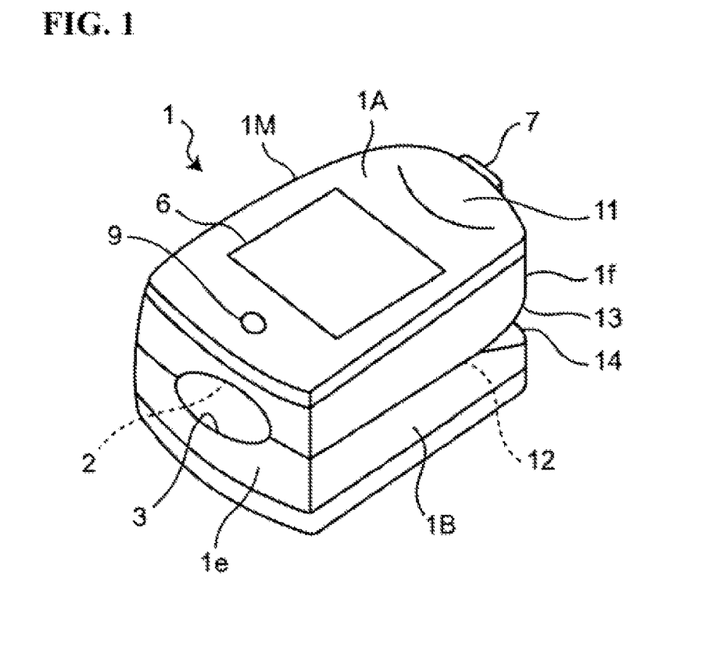
FIG. 1 is a perspective view illustrating the external appearance of a pulse oximeter embodying a biological information measurement device according to this invention.

FIG. 1 illustrates, from an angle, the external appearance of a fingertip clip-type pulse oximeter 1 embodying a biological information measurement device according to this invention. In the following descriptions, "up", "down", "top surface", "bottom surface", "front side", "rear side", and so on are simply terms for more easily describing the external appearance of the pulse oximeter 1. The pulse oximeter 1 can be attached to a fingertip, which serves as a measurement area of a measurement subject, with any orientation.

The pulse oximeter 1 includes a main body 1M that forms a casing. The main body 1M has a main body upper portion 1A and a main body lower portion 1B disposed on the top and bottom, respectively. A finger insertion hole 3 into which the fingertip of the measurement subject (the measurement area) is to be inserted during measurement is formed in an end portion 1e on the front side of the main body 1M, between and as a part of the main body upper portion 1A and the main body lower portion 1B. In this example, the finger insertion hole 3 is a hole that has an approximately oval-shaped cross-section and that extends into the interior of the main body 1M; an internal sensor 2 is provided within the finger insertion hole 3 as a first sensor.

A display unit 6 for displaying biological information and an operating unit 9 to be operated by a user (typically a measurement subject) are provided in the top surface of the main body upper portion 1A. A connector 7 is provided in a rear side end portion of the main body upper portion 1A. The constituent elements 2, 6, 7, and 9 will be described later.

Mutually-opposing surfaces of the main body upper portion 1A and the main body lower portion 1B form tapered faces 13 and 14 that are increasingly distanced from each other as the portions progress toward the rear side are formed near a rear side end portion if of the main body 1M. A hinge 12 that connects the main body upper portion 1A and the main body lower portion 1B is provided at an area where the tapered faces 13 and 14 converge. The main body upper portion 1A and the main body lower portion 1B are capable of pivoting relative to each other central to the hinge 12. Furthermore, the main body upper portion 1A and the main body lower portion 1B receive a biasing force from a spring, which is not shown, so that the sides thereof at the end portion 1e move toward each other central to the hinge 12. Thus the main body upper portion 1A and the main body lower portion 1B make contact with each other on the sides thereof at the end portion 1e when there is no external force on the main body 1M.

An indentation 11 for making it easier for the measurement subject to insert his/her fingertip into the finger insertion hole 3 is provided in the top surface of the main body upper portion 1A, near the rear side end portion 1f.

Figure 2:
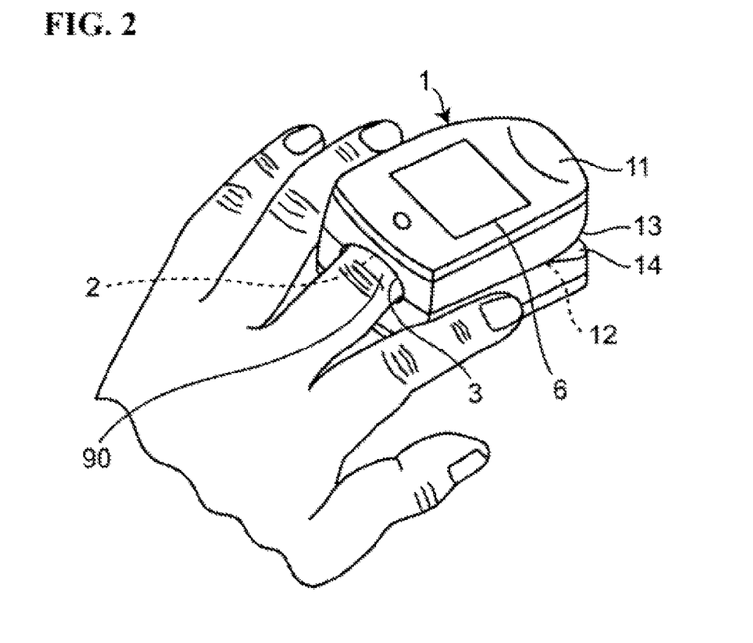
FIG. 2 is a diagram illustrating an example of a normal state in which the stated pulse oximeter is used.

During use, the measurement subject places, for example, the thumb of his/her right hand on the indentation 11 and places the index finger of his/her right hand against the bottom surface of the main body lower portion 1B and applies a compressing force from above and below the main body upper portion 1A and the main body lower portion 1B, respectively. Upon doing so, the main body upper portion 1A and the main body lower portion 1B pivot central to the hinge 12 so that the tapered faces 13 and 14 approach each other, while the main body upper portion 1A and the main body lower portion 1B separate on the end portion 1e side. As a result, the finger insertion hole 3 opens wide, and the measurement subject can easily insert a fingertip on his/her left hand into the finger insertion hole 3. When the measurement subject releases the fingers of his/her right hand from the main body 1M while the fingertip of his/her left hand is in the finger insertion hole 3, a fingertip 90 (the fingertip of the middle finger, in this example) of the left hand is inserted in the finger insertion hole 3 and is held between the main body upper portion 1A and the main body lower portion 1B by the restorative force of the stated spring, as illustrated in FIG. 2. In other words, the main body 1M is attached to the fingertip 90 and the internal sensor 2 opposes the fingertip 90.

In this sense, the main body upper portion 1A, the main body lower portion 1B, the hinge 12, and the stated spring constitute a clip portion that holds the fingertip 90 serving as the measurement area.

Figure 3:
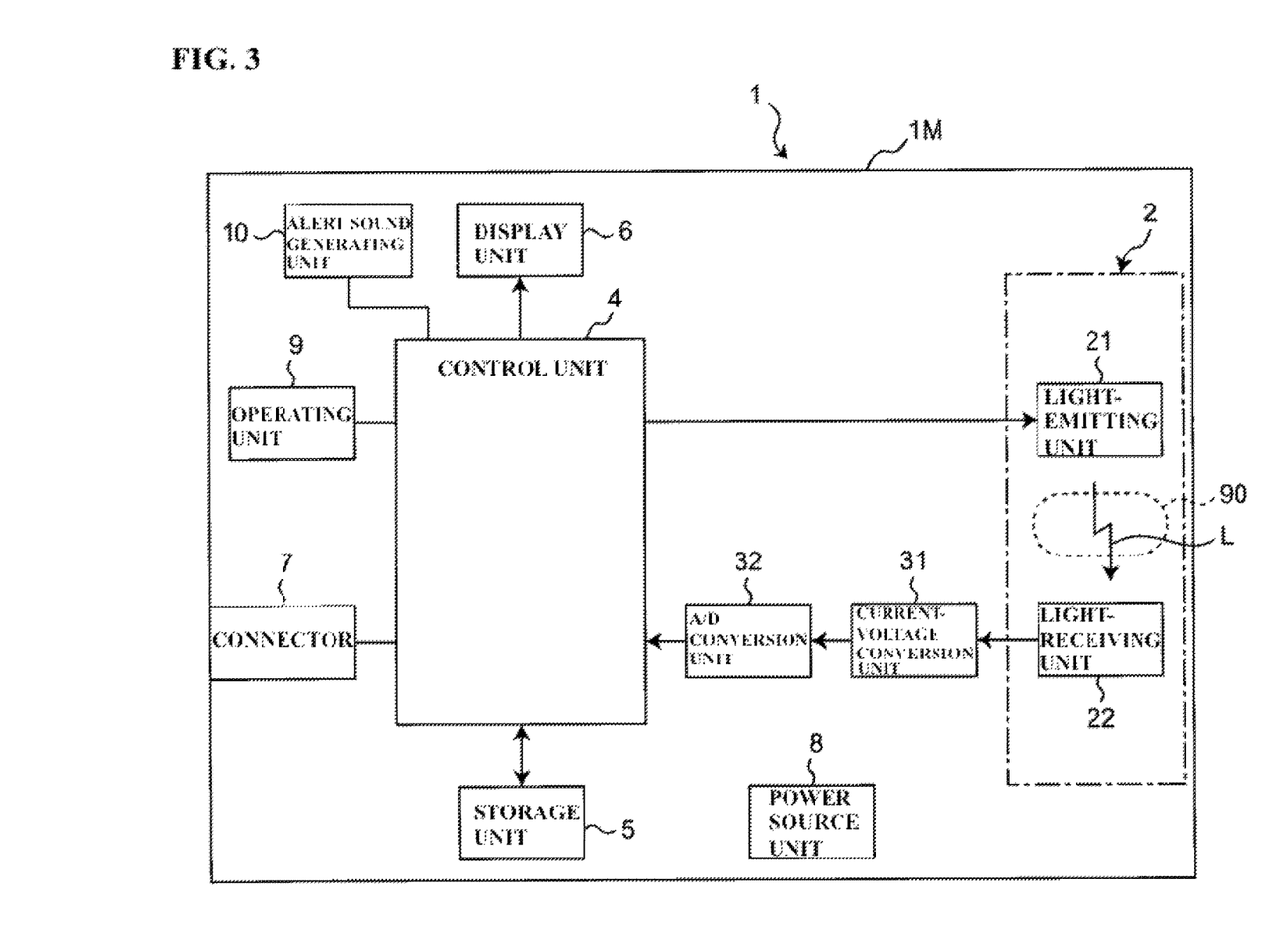
FIG. 3 is a diagram illustrating a functional block configuration of the stated pulse oximeter.

FIG. 3 is a diagram illustrating a functional block configuration of the pulse oximeter 1. The pulse oximeter 1 includes the internal sensor 2 serving as the first sensor, a current-voltage conversion unit 31, an A/D conversion unit 32, a control unit 4, a storage unit 5, the display unit 6, the connector 7, a power source unit 8, and an alert sound generating unit 10, which are provided integrally with the main body 1M.

The internal sensor 2 has a light-emitting unit 21 that emits light L toward the fingertip 90, and a light-receiving unit 22 that receives the light L that has passed through the fingertip 90 and generates a current (that is, is a transmissive type). Through this, the internal sensor 2 detects signals expressing a transdermal oxygen saturation level ($SpO_2$) in arterial blood, a pulse rate (BPM (Beats Per Minute)), and a perfusion index (PI) from the fingertip 90.

Figure 4:
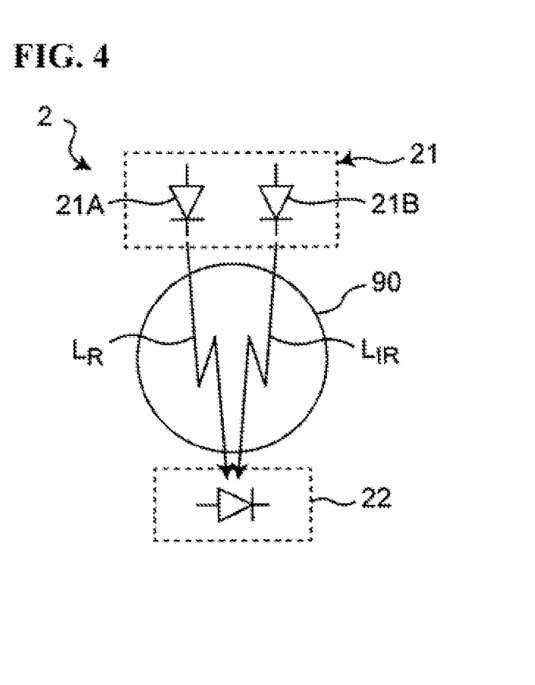
FIG. 4 is a diagram illustrating the configuration of an internal sensor serving as a first sensor included in the stated pulse oximeter.

More specifically, as illustrated in FIG. 4, the internal sensor 2 has a light-emitting diode 21A that emits red light $L_R$ at a wavelength of 660 (nm) in this example, and a light-emitting diode 21B that emits infrared light $L_{IR}$ at a wavelength of 940 (nm) in this example. The light-receiving unit 22 employs a silicon photodiode, and generates a current based on an intensity of the received light.

Here, hemoglobin in the blood has different light absorbances for the red light $L_R$ and the infrared light $L_R$ depending on whether or not there are bonds with oxygen. The internal sensor 2 detects a signal expressing the transdermal oxygen saturation level $SpO_2$ in arterial blood using such differences in the light absorbance properties of hemoglobin lacking oxygen (reduced) and hemoglobin having oxygen (oxygenated) with respect to the red light $L_R$ and the infrared light $L_{IR}$ (a two-wavelength blood light absorbance technique). Note that a component that passes through arterial blood and a component that passes through venous blood, soft tissue, and so on are distinguished using the concept that an AC component of the signal detected by the sensor (a pulsation component) is produced by the arterial blood.

The pulse rate BPM is in this example found by counting the pulsation component.

The perfusion index PI uses a ratio between the AC component (pulsation component) and a DC component (non-pulsation component) of the signal detected by the sensor, and is defined as PI (%)=(pulsation component)/(non-pulsation component)×100. As described above, the PI normally has a value within a range of 0.02% to 20%, and greater than or equal to 1% is considered a desirable value.

The current-voltage conversion unit 31 illustrated in FIG. 3 converts the current outputted by the internal sensor 2 (and more precisely, the light-receiving unit 22) into a voltage.

The A/D conversion unit 32 converts an analog signal (the voltage) outputted by the current-voltage conversion unit 31 into a digital signal and outputs the digital signal to the control unit 4.

The control unit 4 includes a CPU (Central Processing Unit) that operates in accordance with software, and controls the overall operations of the pulse oximeter 1.

The storage unit 5 includes a RAM (Random Access Memory) used as a work region required by the control unit 4 to execute programs, and a ROM (Read-only Memory) for storing programs to be executed by the control unit 4. The storage unit 5 also stores signals outputted by the internal sensor 2 (and an external sensor 81, which will be described later), information obtained by processing those signals, and so on in time series throughout a given period.

The display unit 6 is in this example constituted by an LCD (Liquid Crystal Display) or an EL (Electroluminescence) display. The display unit 6 displays the transdermal oxygen saturation level $SpO_2$ in the arterial blood, the pulse rate BPM, and the perfusion index PI obtained as measurement results, as well as other types of information such as messages, which will be described later.

The operating unit 9 is in this example constituted by a push-button switch (a power on button). In other words, when the measurement subject presses the push-button switch 9, the pulse oximeter 1 is turned on or off.

The power source unit 8 is constituted by a dry cell battery (not shown; two AAA batteries, in this example), and when the push-button switch 9 is turned on, power is supplied to the respective units of the pulse oximeter 1 from the dry cell battery. Note that the power source unit 8 may have a power-off function that automatically stops the supply of power when a pulsation is not detected for a set amount of time.

Figure 5:
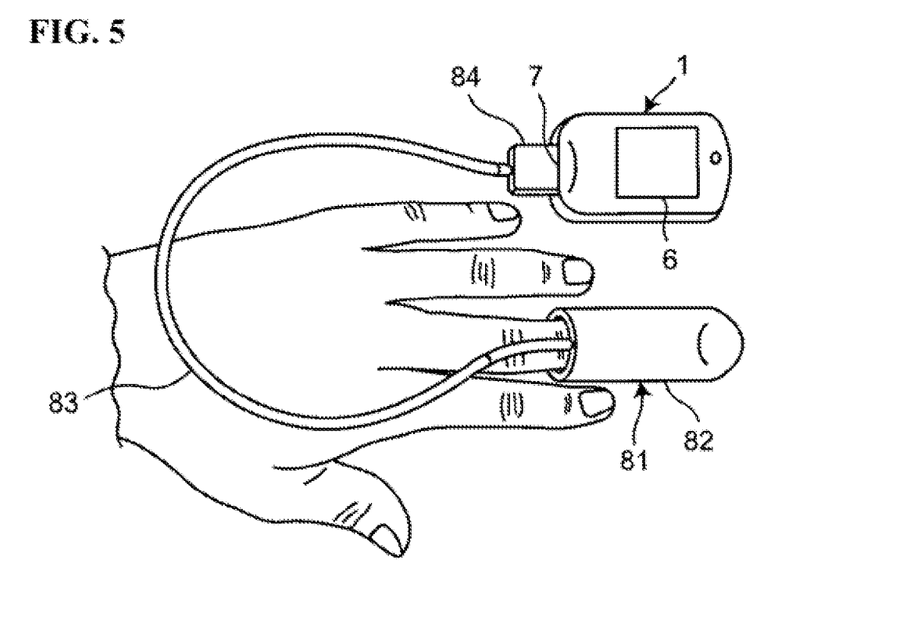
FIG. 5 is a diagram illustrating measurement using a sensor that is external to the stated main body.

The connector 7 is in this example constituted by a USB (Universal Serial Bus) connector, and is used for connecting the external sensor 81, which serves as a second sensor. As illustrated in FIG. 5, the external sensor 81 includes a cylindrical sensor portion 82 that is separate from the main body 1M and into which a fingertip is inserted, a USB cable 83 connected to the sensor portion 82, and a USB connector 84 provided at an end portion of the USB cable 83 (an end portion of the side opposite from the sensor portion 82). The sensor portion 82 is communicably connected to the connector 7 of the main body 1M via the USB cable 83 and the USB connector 84. The sensor portion 82 has the same transmissive-type configuration as the internal sensor 2 illustrated in FIG. 4, and obtains a signal expressing biological information from the fingertip, which serves as a measurement area. A pressurizing force applied to the fingertip by the sensor portion 82 is smaller than the pressurizing force (holding pressure) applied to the fingertip by the main body 1M. The sensor portion 82 is thus suited to measuring the $SpO_2$ of a patient having a serious condition such as hypoperfusion, for example.

The alert sound generating unit 10 is in this example constituted by a buzzer, and generates a buzzer sound in response to an instruction from the control unit 4 when the fingertip has been properly inserted into the internal sensor 2 (or the external sensor 81) or has been removed therefrom. Accordingly, the buzzer sound enables the measurement subject to know that he/she is correctly operating the pulse oximeter 1.

Figure 6:
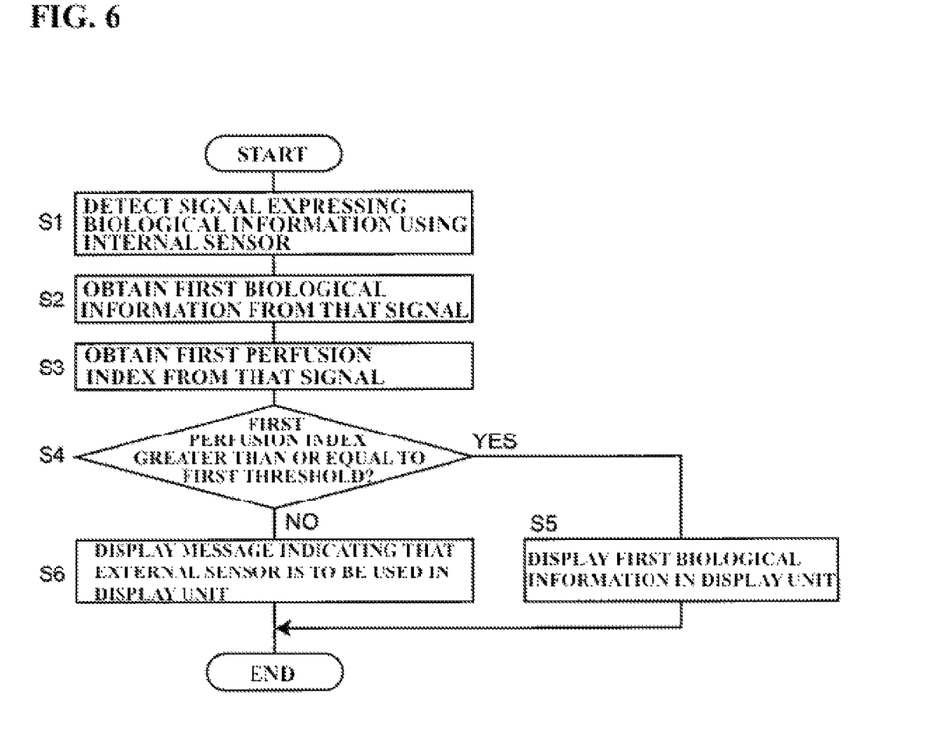
FIG. 6 is a diagram illustrating a flow of measurement performed by the stated pulse oximeter.

FIG. 6 illustrates an example of a measurement flow performed by the pulse oximeter 1.

i) When the fingertip 90 is inserted into the finger insertion hole 3 as illustrated in FIG. 2, first, in step S1 of FIG. 6, the internal sensor 2 detects a signal expressing biological information from the fingertip 90. The signal detected by the internal sensor 2 is inputted into the control unit 4 via the current-voltage conversion unit 31 and the A/D conversion unit 32 illustrated in FIG. 3.

ii) In step S2 of FIG. 6, the control unit 4 functions as a first biological information obtainment unit, processing the signal from the internal sensor 2 (the signal inputted via the current-voltage conversion unit 31 and the A/D conversion unit 32) and obtaining first biological information VT1 from the fingertip 90. In this example, the first biological information VT1 includes the $SpO_2$ value and the pulse rate, and not the perfusion index PI. The obtained first biological information VT1 is stored in the storage unit 5.

iii) In step S3 of FIG. 6, the control unit 4 functions as a first perfusion index obtainment unit, obtaining a first perfusion index PI1 from the stated signal. The first perfusion index PI1 is found according to the definition given above, using the ratio between the AC component (pulsation component) and the DC component (non-pulsation component) of the signal detected by the internal sensor 2, and is found as PI1 (%)=(pulsation component)/(non-pulsation component)×100.

Note that the first perfusion index PI1 in step S3 may also be obtained in parallel with the first biological information VT1 in step S2 or may be obtained prior thereto.

iv) In step S4 of FIG. 6, the control unit 4 functions as a first determining unit, determining whether or not the first perfusion index PI1 is greater than or equal to a first threshold (indicated by reference numeral α1).

The first threshold α1 for the first perfusion index PI1 is set based on a pre-confirmed result in which an accurate measurement is obtained by the internal sensor 2 when the index is greater than or equal to the first threshold α1. In this example, α1 is assumed to be fixed at 0.3%.

v) Here, the first biological information VT1 is considered to be accurate in the case where the first perfusion index PI1 is greater than or equal to the first threshold α1 (YES in step S4). In this case, in step S5, the control unit 4 reads out the first biological information VT1 from the storage unit 5 and permits the first biological information VT1 to be displayed in the display unit 6.

Figure 7:
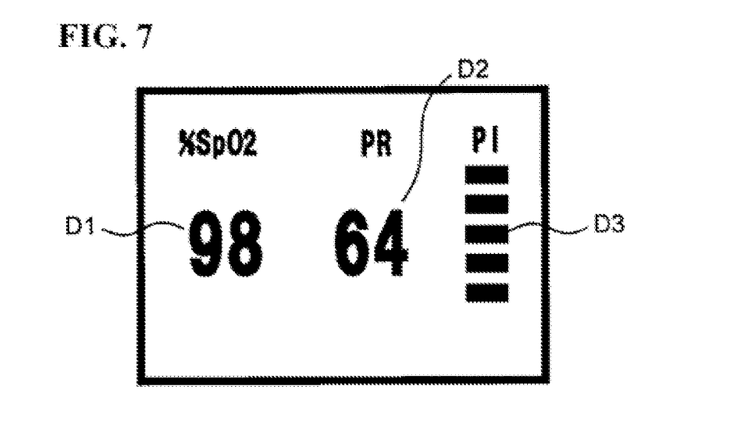
FIG. 7 is a diagram illustrating an example of a normal display in a display unit of the stated pulse oximeter.

As a result, as indicated by the example illustrated in FIG. 7, the $SpO_2$ value (98%, in this example) and the pulse rate (64 BPM, in this example) are respectively displayed as the first biological information VT1 in predefined display areas D1 and D2 of the display unit 6.

Meanwhile, in this example, the first perfusion index PI1 is displayed as an indicator in a predefined display area D3 of the display unit 6 along with the $SpO_2$ value and pulse rate. This indicator display expresses the magnitude of the PI as a number of lamps arranged in a height direction (indicated in FIG. 7 by a row of five black rectangles) that are lit. In this example, the first perfusion index PI1 is sufficiently higher than the first threshold α1, and thus all five lamps are lit.

Accordingly, the user can know the accurate $SpO_2$ value, pulse rate, and perfusion index PI level by viewing the details displayed in the display unit 6.

vi) On the other hand, the first biological information VT1 is considered to be inaccurate in the case where the first perfusion index PI1 is less than the first threshold α1 (NO in step S4 of FIG. 6). In this case, in step S6, the control unit 4 prohibits the display of the $SpO_2$ value and the pulse rate in the display unit 6. In this example, dash marks "--" are displayed in the display areas D1 and D2 of the display unit 6 instead of the $SpO_2$ and pulse rate values, as in the example illustrated in FIG. 8. Accordingly, the user will no longer be caused to make an error in his/her judgment by inaccurate biological information.

Figure 8:
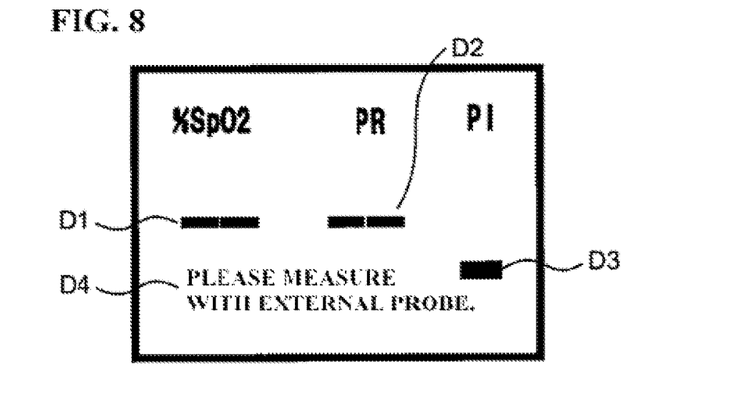
FIG. 8 is a diagram illustrating an example of a message displayed in the stated display unit when displaying first biological information (a $SpO_2$ value, a pulse rate) detected using an internal sensor serving as a first sensor is prohibited.

In addition to this, the control unit 4 carries out control for displaying, in the display unit 6, an indication that the external sensor 81 is to be used. In this example, "please measure with external probe" is displayed in a predefined display area D4 of the display unit 6 as a message indicating that the external sensor 81 is to be used, as illustrated in FIG. 8. The user is therefore prompted by this message to take a measurement using the external sensor 81. Note that when making this notification, the control unit 4 may cause the alert sound generating unit 10 to emit a buzzer sound in order to draw the user's attention to the message. This enables the user to easily recognize that there has been a notification and confirm the details of the notification.

Furthermore, the control unit 4 displays only a single lamp (indicated in FIG. 8 by a single black rectangle) in the display area D3 of the display unit 6. Accordingly, the user can recognize that the reason the message is displayed is that the perfusion index PI (the first perfusion index PI1, here) is low.

Having been prompted by the message in the display area D4 to take a measurement using the external sensor 81, the user connects the external sensor 81 to the main body 1M and attaches the external sensor 81 to the fingertip 90, as illustrated in FIG. 5. A measurement is taken using the external sensor 81 as a result.

As described earlier, the external sensor 81 interferes with perfusion in the fingertip less than the internal sensor 2. Accordingly, more accurate biological information can be measured.

Note that the notification made in step S6 of FIG. 6 is not limited to a message displayed by the display unit 6 and/or a buzzer sound. A graphic indicating that the external sensor 81 is to be used (for example, a diagram expressing a shape of the external sensor 81) may be displayed in the display unit 6 instead of or in addition to the message. In addition, the notification may be made using audio (for example, a voice that says the aforementioned "please measure with external probe") instead of the buzzer sound generated by the alert sound generating unit 10.

Figure 10:
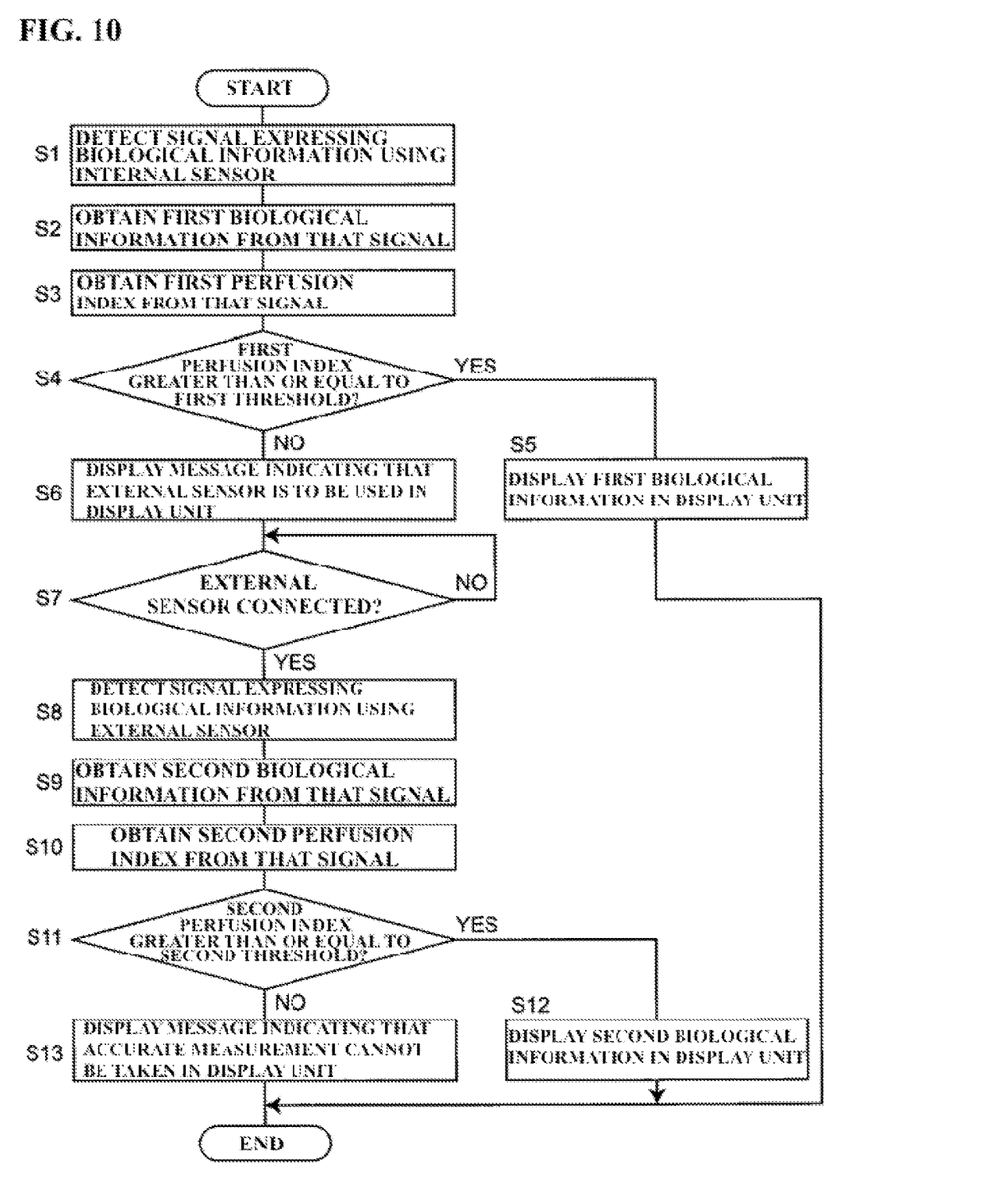
FIG. 10 is a diagram illustrating another flow of measurement performed by the stated pulse oximeter.

FIG. 10 illustrates another flow of the measurement performed by the pulse oximeter 1. In this measurement flow, steps S1 to S6 follow exactly the same processing as that of the measurement flow illustrated in FIG. 6. The following processing is carried out thereafter.

vii) In step S7 of FIG. 10, the control unit 4 functions as a connection detecting unit, detecting whether or not the external sensor 81 has been connected to the main body 1M. In the case where the external sensor 81 is not connected (NO in step S7), the control unit 4 stands by until a connection is made.

viii) When the external sensor 81 is connected to the main body 1M as illustrated in FIG. 5 (YES in step S7) and the fingertip 90 is inserted into the sensor portion 82 of the external sensor 81, in step S8 of FIG. 10, the external sensor 81 detects a signal expressing biological information from the fingertip 90. The signal detected by the external sensor 81 is inputted into the control unit 4.

ix) In step S9 of FIG. 10, the control unit 4 functions as a second biological information obtainment unit, processing the signal from the external sensor 81 and obtaining second biological information VT2 of the fingertip 90. In this example, the second biological information VT2 includes the $SpO_2$ value and the pulse rate, and not the perfusion index PI. The obtained second biological information VT2 is stored in the storage unit 5.

x) In step S10 of FIG. 10, the control unit 4 functions as a second perfusion index obtainment unit, obtaining a second perfusion index PI2 from the stated signal. The second perfusion index PI2 is found according to the definition given above, using the ratio between the AC component (pulsation component) and the DC component (non-pulsation component) of the signal detected by the external sensor 81, and is found as PI2 (%)=(pulsation component)/(non-pulsation component)×100.

Note that the second perfusion index PI2 in step S10 may also be obtained in parallel with the second biological information VT2 in step S9 or may be obtained prior thereto.

xi) In step S11 of FIG. 10, the control unit 4 functions as a second determining unit, determining whether or not the second perfusion index PI2 is greater than or equal to a second threshold (indicated by reference numeral α2).

The second threshold α2 for the second perfusion index PI2 is set based on a pre-confirmed result in which an accurate measurement is obtained by the external sensor 81 when the index is greater than or equal to the second threshold α2. In this example, α2 is assumed to be fixed at 0.3%.

xii) Here, the second biological information VT2 is considered to be accurate in the case where the second perfusion index PI2 is greater than or equal to the second threshold α2 (YES in step S11). In this case, in step S12, the control unit 4 reads out the second biological information VT2 from the storage unit 5 and permits the second biological information VT2 to be displayed in the display unit 6.

As a result, as with the example illustrated in FIG. 7, the $SpO_2$ value (98%, in this example) and the pulse rate (64 BPM, in this example) are respectively displayed as the second biological information VT2 in the display areas D1 and D2 of the display unit 6.

Meanwhile, in this example, the second perfusion index PI2 is displayed as an indicator in the display area D3 of the display unit 6 along with the $SpO_2$ value and pulse rate. In this example, the second perfusion index PI2 is sufficiently higher than the second threshold α2, and thus all five lamps are lit.

Accordingly, the user can know the accurate $SpO_2$ value, pulse rate, and perfusion index PI level by viewing the details displayed in the display unit 6.

xiii) On the other hand, the second biological information VT2 is considered to be inaccurate in the case where the second perfusion index PI2 is less than the second threshold α2 (NO in step S11 of FIG. 10). In this case, in step S13, the control unit 4 prohibits the display of the $SpO_2$ value and the pulse rate in the display unit 6. In this example, dash marks "--" are displayed in the display areas D1 and D2 of the display unit 6 instead of the $SpO_2$ and pulse rate values, as in the example illustrated in FIG. 9. Accordingly, the user will no longer be caused to make an error in his/her judgment by inaccurate biological information.

Figure 9:
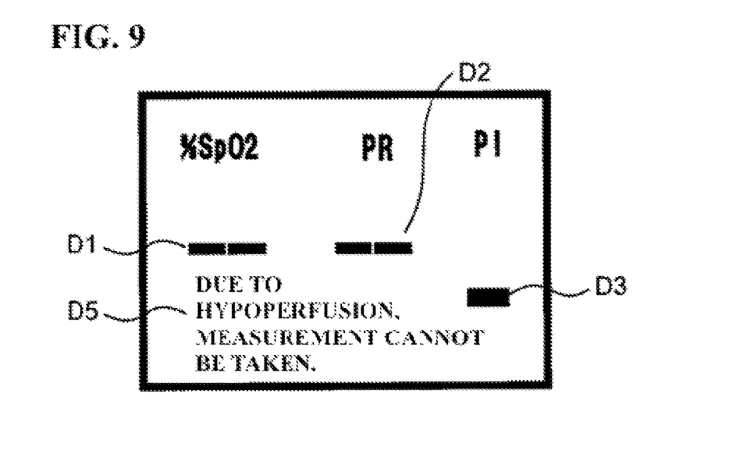
FIG. 9 is a diagram illustrating an example of a message displayed in the stated display unit when displaying second biological information (a $SpO_2$ value, a pulse rate) detected using an external sensor serving as a second sensor is prohibited.

In addition to this, the control unit 4 carries out control for displaying, in the display unit 6, an indication that an accurate measurement cannot be taken. In this example, as indicated in FIG. 9, a message reading "due to hypoperfusion, measurement cannot be taken" is displayed in a display area D5 of the display unit 6 (the same area as the display area D4 illustrated in FIG. 8) as a message indicating that an accurate measurement cannot be taken. Accordingly, by viewing this message, the user can know that accurate biological information cannot be obtained from the fingertip 90 for that measurement subject (for example, a patient having a serious level of poor peripheral circulation). Note that the control unit 4 may cause the alert sound generating unit 10 to emit a buzzer sound in order to draw the user's attention to the message. This enables the user to easily recognize that there has been a notification and confirm the details of the notification.

Furthermore, the control unit 4 displays only a single lamp (indicated in FIG. 9 by a single black rectangle) in the display area D3 of the display unit 6. Accordingly, the user can recognize that the reason the message is displayed is that the perfusion index PI (the second perfusion index PI2, here) is low.

Note that the notification made in step S13 of FIG. 10 is not limited to a message displayed by the display unit 6 and/or a buzzer sound. A graphic indicating that an accurate measurement cannot be taken (for example, an x or the like) may be displayed in the display unit 6 instead of or in addition to the message. In addition, the notification may be made using audio (for example, a voice that says the aforementioned "due to hypoperfusion, measurement cannot be taken") instead of the buzzer sound generated by the alert sound generating unit 10.

Although the thresholds α1 and α2 are fixed at 0.3% in the aforementioned example, the invention is not limited thereto. The thresholds α1 and α2 may be set to be variable. For example, the thresholds α1 and α2 may be set lower than 0.3% in a variable manner, such as 0.2%, 0.1%, 0.05%, 0.02%, and so on, as long as the $SpO_2$ value and the pulse rate can be measured accurately, for example. The first threshold α1 and the second threshold α2 may also be set to different values. For example, α1 may be set to be greater than α2, with α1=0.3% and α2=0.1% for example, as long as the $SpO_2$ value and the pulse rate can be measured more accurately when using the external sensor 81 than when using the internal sensor 2.

Furthermore, as described earlier, the external sensor 81 (and more precisely, the sensor portion 82) interferes with perfusion in the fingertip less than the internal sensor 2. Accordingly, the second biological information VT2 obtained using the external sensor 81 can be expected to be more accurate than the first biological information VT1 obtained using the internal sensor 2. Accordingly, in the measurement flow illustrated in FIG. 10, step S10 (obtaining the second perfusion index PI2), step S11 (determining whether or not the second perfusion index PI2 is greater than or equal to the second threshold α2), and step S13 (displaying a message indicating that an accurate measurement cannot be taken) may be omitted, and the process of step S12 (displaying the $SpO_2$ value and the pulse rate as the second biological information VT2 and displaying the second perfusion index PI2) may be carried out without exception following step S9 (obtaining the second biological information VT2).

Figure 11:
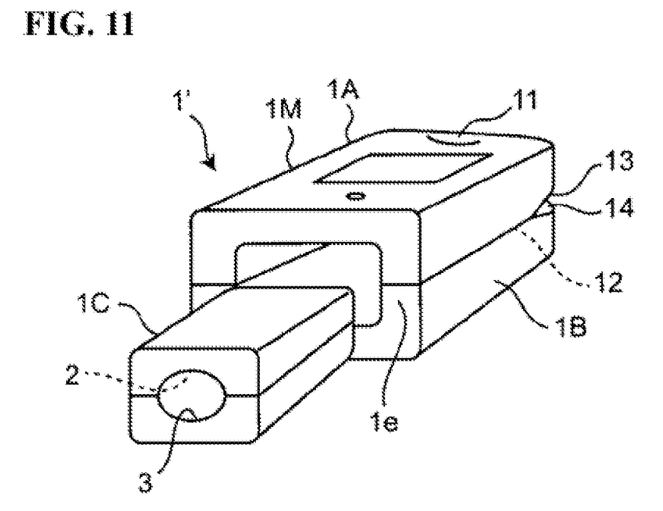
FIG. 11 is a diagram illustrating a state in which the stated internal sensor is provided so as to be removable from the stated main body.

Although a notification that the external sensor 81 is to be used is made (step S6 in FIG. 6 and FIG. 10) when it is determined that the first perfusion index PI1 is less than the first threshold α1 (NO in step S4 of FIG. 6 in FIG. 10), the invention is not limited thereto. For example, as illustrated in FIG. 11, a part 1C that includes the internal sensor 2 may be provided so as to be removable from the main body 1M. Then, a notification indicating that the internal sensor 2 is to be removed from the main body 1M and used is made in step S6 of FIG. 6 in FIG. 10, instead of a message indicating that the external sensor 81 is to be used. Accordingly, the notification prompts the user to remove the part 1C including the internal sensor 2 from the main body 1M and use the sensor in that state. The part 1C including the internal sensor 2 is lighter than the main body 1M as a whole, and thus little pressure is put on the fingertip that serves as the measurement area, which in turn does not interfere significantly with perfusion. Accordingly, taking a measurement using the part 1C including the internal sensor 2 that has been removed from the main body 1M enables a more accurate measurement than in the case where a measurement is taken with the internal sensor 2 remaining attached to the main body 1M.

Although the internal sensor 2 and the external sensor 81 are described as being of the transmissive type in the aforementioned example, the invention is not limited thereto. One or both of the internal sensor 2 and the external sensor 81 may be a reflective type. In a reflective-type configuration, light is emitted from a light-emitting unit onto the measurement area 90, and light reflected by the measurement area 90 is received by a light-receiving unit.

In addition, although the communication connection between the external sensor 81 (the sensor portion 82) serving as the second sensor and the main body 1M is described as being a wired connection using the cable 83, the invention is not limited thereto. The second sensor may be connected to the main body 1M wirelessly.

In addition, although the pulse oximeter 1 does not include any particular communication unit in the aforementioned example, the invention is not limited thereto. The pulse oximeter 1 may include a communication unit provided integrally with the main body 1M, and data obtained as measurement results may then be sent to a mobile terminal, a personal computer, a server, or the like over a network.

In addition, although the main body 1M of the pulse oximeter 1 is described as holding a fingertip that serves as the measurement area in the above example, the invention is not limited thereto. The present invention can be broadly applied in biological information measurement devices including, in a main body that is to be attached to a measurement area (not limited to a fingertip), a sensor that detects a signal expressing biological information from the stated measurement area.

The aforementioned embodiments are merely examples, and many variations thereon can be carried out without departing from the scope of this invention.

REFERENCE SIGNS LIST 1 biological information measurement device
1M main body
2 internal sensor
6 display unit
81 external sensor

The invention claimed is:

1. A biological information measurement device comprising:
    a main body that is to be attached to a measurement area;
    an internal sensor that is provided internally in the main body and detects a signal expressing biological information including at least transdermal oxygen saturation level in arterial blood from the measurement area;
    a display unit configured to display biological information;
    a connector included in the main body and configured to be connected with an external sensor that is external to the main body, the external sensor detecting, when the external sensor is connected to the main body, a signal expressing biological information including at least transdermal oxygen saturation level in arterial blood from the measurement area; and
    a control unit that defines and functions as:
        a first perfusion index obtainment unit that obtains a first perfusion index expressing a ratio between a pulsation component and a non-pulsation component of arterial blood in the measurement area based on the signal detected by the internal sensor;
        a first biological information obtainment unit that obtains first biological information of the measurement area, aside from the first perfusion index, by processing the signal detected by the internal sensor; and
        a first determining unit that determines whether or not the first perfusion index is greater than or equal to a first threshold; wherein
    the control unit carries out control for permitting the first biological information to be displayed in the display unit when the first determining unit has determined that the first perfusion index is greater than or equal to the first threshold and carries out control for making a notification that the external sensor is to be used instead of the internal sensor when the first determining unit has determined that the first perfusion index is less than the first threshold.

2. The biological information measurement device according to claim 1,
wherein the control unit prohibits the first biological information from being displayed in the display unit when the first determining unit has determined that the first perfusion index is less than the first threshold.

3. The biological information measurement device according to claim 1,
wherein the control unit displays an indication that the first perfusion index is low in the display unit when the first determining unit has determined that the first perfusion index is less than the first threshold.

4. The biological information measurement device according to claim 1, wherein
the control unit defines and functions as:
a connection detecting unit that detects whether or not the external sensor has been connected to the main body; and
a second biological information obtainment unit that obtains second biological information of the measurement area by processing the signal detected by the external sensor from the measurement area when the external sensor has been connected to the main body; and
when the second biological information has been obtained by the second biological information obtainment unit, the control unit permits the second biological information to be displayed in the display unit.

5. The biological information measurement device according to claim 1, wherein
the control unit defines and functions as:
a connection detecting unit that detects whether or not the external sensor has been connected to the main body;
a second perfusion index obtainment unit that obtains a second perfusion index expressing a ratio between a pulsation component and a non-pulsation component of arterial blood in the measurement area based on the signal detected by the external sensor from the measurement area when the external sensor has been connected to the main body;
a second biological information obtainment unit that obtains second biological information of the measurement area, aside from the second perfusion index, by processing the signal detected by the external sensor; and
a second determining unit that determines whether or not the second perfusion index is greater than or equal to a second threshold, and
the control unit carries out control for permitting the second biological information to be displayed in the display unit when the second determining unit has determined that the second perfusion index is greater than or equal to the second threshold and carries out control for making a notification that an accurate measurement cannot be taken when the second determining unit has determined that the second perfusion index is less than the second threshold.

6. The biological information measurement device according to claim 5,
wherein the control unit prohibits the second biological information from being displayed in the display unit when the second determining unit has determined that the second perfusion index is less than the second threshold.

7. The biological information measurement device according to claim 5,
wherein the control unit displays an indication that the second perfusion index is low in the display unit when the second determining unit has determined that the second perfusion index is less than the second threshold.

8. The biological information measurement device according to claim 1,
wherein the notification is a display of a message or a graphic in the display unit and/or a buzzer sound or audio.

9. The biological information measurement device according to claim 1, wherein the connector is configured to connect to the external sensor which applies a pressurizing force to the measurement area that is less than a pressurizing force applied to the measurement area by the main body that includes the internal sensor.

* * * * *